(12) United States Patent
Chen et al.

(10) Patent No.: US 8,802,737 B2
(45) Date of Patent: Aug. 12, 2014

(54) METHOD FOR IMPROVING TETRACYCLINE-RESISTANCE OF *ACINETOBACTER BAUMANNII*

(71) Applicant: Kaohsiung Medical University, Kaohsiung (TW)

(72) Inventors: Yen-Hsu Chen, Kaohsiung (TW); Hui-Min Wang, Kaohsiung (TW); Chung-Yi Chen, Kaohsiung (TW); Hsi-An Chen, Kaohsiung (TW); Wei-Ru Lin, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 14/028,960

(22) Filed: Sep. 17, 2013

(65) Prior Publication Data
US 2014/0018324 A1 Jan. 16, 2014

Related U.S. Application Data

(62) Division of application No. 13/042,065, filed on Mar. 7, 2011, now abandoned.

(51) Int. Cl.
| | |
|---|---|
| *A01N 35/00* | (2006.01) |
| *A61K 31/12* | (2006.01) |
| *A01N 31/00* | (2006.01) |
| *A61K 31/045* | (2006.01) |
| *A01N 31/08* | (2006.01) |
| *A61K 31/05* | (2006.01) |
| *A61K 31/65* | (2006.01) |

(52) U.S. Cl.
CPC .............. *A61K 31/12* (2013.01); *A61K 31/65* (2013.01)
USPC ............................ 514/678; 514/724; 514/731

(58) Field of Classification Search
CPC ...................................................... A61K 31/05
USPC ................................. 514/154, 678, 724, 731
See application file for complete search history.

(56) References Cited

U.S. PATENT DOCUMENTS

| | | |
|---|---|---|
| 5,476,669 A | 12/1995 | Borody |
| 6,264,926 B1 | 7/2001 | Farooqi et al. |
| 7,658,942 B2 | 2/2010 | Deckner et al. |
| 7,736,629 B2 | 6/2010 | Kamath et al. |
| 2006/0204467 A1 | 9/2006 | Littau et al. |

FOREIGN PATENT DOCUMENTS

TW 200918085 5/2009

OTHER PUBLICATIONS

Wang, Hui-Min, et al., "Zingiber officinale (Ginger) Compounds Have Tetracycline-resistance Modifying Effects Against Clinical Extensively Drug-Resistant *Acinetobacter baumannii*", Phytotherapy Research, Jun. 17, 2010, pp. 1825-1830, vol. 24, Published in Wiley Online Library(DOI:10.1002/ptr.3201).

*Primary Examiner* — Yong Chong
(74) *Attorney, Agent, or Firm* — Muncy, Geissler, Olds & Lowe, P.C.

(57) ABSTRACT

A method for improving tetracycline-resistance of *A. baumannii*, by providing a ginger compound combined with tetracycline to against *A. baumannii* infection, wherein the ginger compound comprises [6]-dehydrogingerdione, [6]-shogaol and [6]-gingerol or [10]-gingerol, [6]-shogaol and [6]-gingerol.

6 Claims, 1 Drawing Sheet

METHOD FOR IMPROVING TETRACYCLINE-RESISTANCE OF *ACINETOBACTER BAUMANNII*

CROSS REFERENCE TO RELATED APPLICATIONS

This is a divisional application of U.S. patent application Ser. No. 13/042,065 filed on Mar. 7, 2011.

BACKGROUND OF THE INVENTION

1. Field of the Invention

The present invention relates to a medication for bacterial infection particularly to a medication for extensively drug resistant *Acinetabacter baumannii.*

2. Description of the Related Art

*Acinetobacter baumannii*, as referred to a non-enteric gram-negative bacillus, is a common pathogenic bacterium generally leading to severe pneumonia, sepsis, and various infections on urinary tract and respiratory tract. Since 1980s, an increasing amount of antibiotics has been used on *A. baumannii* infection. The *A. baumannii* tends to show multiple drug-resistance to most commercial antibiotics, including penicillins, cephalosporins, monobactam, aminoglycosides, carbapenems, sulbactam and fluroroquinolones. Accordingly, drug resistant *A. baumannii* has becomes a major cause of nosocomal infection, and which always results in serious mortality, especially in intensive care units due to the lack of proper antimicrobials.

In recent decades, since the drug-resistance getting controversial, natural components and plant extracts have reported to play an important role in antimicrobial approaches. Referring to U.S. Pat. No. 6,264,926, entitled with "FORMULATION USEFUL AS A NATURAL HERBAL TOOTH POWDER" a formulation of herbal toothpowder or toothpaste for gums and teeth is disclosed and comprises powder or paste of *Zingiber officinale, Zanthoxvlum armaatum, Santalum album, Spilanthes calva, Pistacia lentiseus, Quercus infectoria, Usnea longissima*, roasted alum and common salt. It is suggested that ginger has generally antimicrobial and anti-inflammatory effects, and which can be used as a general antimicrobial ingredient in various products. However, the conventional invention only points out a general antimicrobial effect of the ginger rather than a specific antimicrobial function on particular pathogen.

With reference to Taiwan Published Patent No. 200918085, entitled with "USE OF A POTENT PRODUCT EXTRACTED FROM RHIZOMES OF *ZINGIBER OFFICINALE* IN TREATING A DISEASE ASSOCIATED WITH *HELICOBACTER PYLORI*" a new medical composition treated of *Helicobacter pylori* is provided and comprises a crude extract from rhizomes of *Zingiber officinale*. It is suggested that with a potent fraction obtained via fractionated steps disclosed in the TW Patent No. 200918085, a disease associated with *H. pylori*, such as gastritis, gastric ulcer and duodenal ulcer can be effectively treated. However, the conventional invention above is useless in clinical drug-resistant problem, also in severe nosocomial infection of *Acinetobacter baumannii*. Hence, there is a pressing need of providing a new medication, as well as a new therapeutic approach for the extensive drug-resistant *Acinetobacter baumannii* worldwide.

SUMMARY OF THE INVENTION

The primary objective of this invention is to provide a medication for *Acinetobacter baumannii* infection, which can treat of clinical extensively drug-resistant *Acinetobacter baumannii* infection.

The secondary objective of this invention is to provide a medication for *Acinetobacter baumannii* infection, so as to prevent from nosocomial infection of *Acinetobacter baumannii.*

Another objective of this invention is to provide a method for improving tetracycline-resistance of *Acinetobacter baumannii*, which can improve serious drug-resistant issue in clinical medicine.

Another objective of this invention is to provide a method for improving tetracycline-resistance of *Acinetobacter baumannii*, so as to effectively inhibit clinical *A. baumannii* infection and prevent from nosocomial infection.

A medication for *Acinetobacter baumannii* infection, comprises tetracycline; and a ginger compound, selecting from a group of [6]-dehydrogingerdione, [10]-gingerol, [6]-shogaol and [6]-gingerol.

A method for improving tetracycline-resistance of *Acinetobacter baumannii*, by providing the ginger compound described above combined with tetracycline to against *A. baumannii* infection.

Further scope of the applicability of the present invention will become apparent from the detailed description given hereinafter. However, it should be understood that the detailed description and specific examples, while indicating preferable embodiments of the invention, are given by way of illustration only, since various more will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 1 is a diagram illustrating the structure of [6]-shogaol in the present invention;

FIG. 2 is a diagram illustrating the structure of [6]-dehydrogingerdione in the present invention;

FIG. 3 is a diagram illustrating the structure of [6]-gingerol in the present invention;

FIG. 4 is a diagram illustrating the structure of [10]-gingerol in the present invention.

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE INVENTION

The present invention relates to a medication for *Acinetobacter baumannii* infection comprising tetracycline and a ginger compound, such as [6]-shogaol, [6]-dehydrogingerdione, [6]-gingerol, and [10]-gingerol. The medication for *Acinetobacter baumannii* infection can significantly suppress *A. baumannii* infection, especially to extensively drug-resistant *Acinetobacter baumannii* infection. With such medication, the severe nosocomial infection of *Acinetobacter baumannii* can be effectively reduced.

Figure 1:
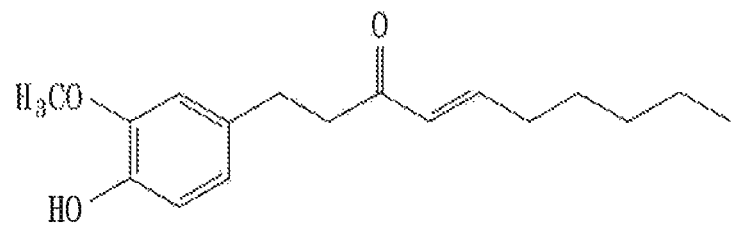
Figure 2:
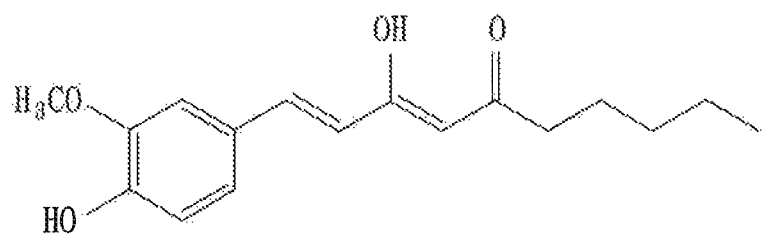
Figure 3:
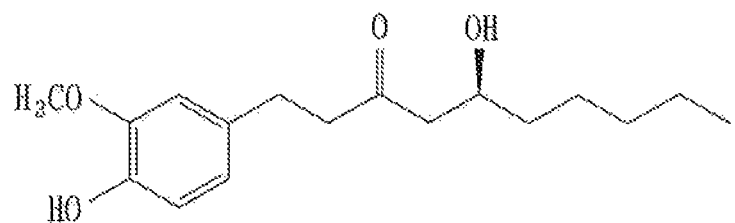
Figure 4:
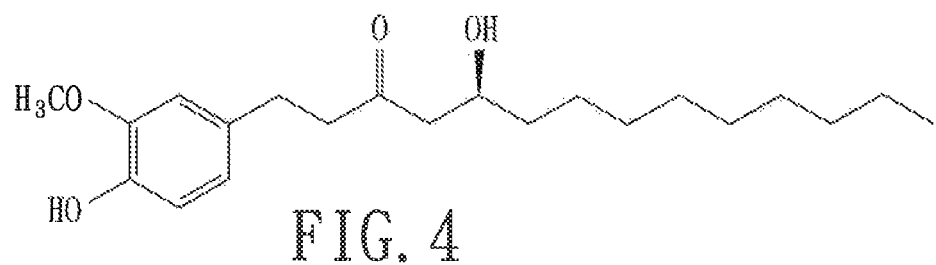

In the present invention, the ginger compound is prepared and mixed with 25 μg/ml of tetracycline, wherein the ginger compound can be one of [6]-shogaol, [6]-dehydrogingerdione, [6]-gingerol, [10]-gingerol, and their composition. In the present embodiment, the ginger compound is extracted from dried and chipped rhizomes of Zingiber officinale with a mixture of $CHCl_3$-MeOH at room temperature, according to a method published by Chen et al. in 2009. With such performance, an extraction is obtained, and further fractionated by silica gel column chromatography with gradients of n-hexane/$CHCl_3$, in order to collect the [6]-shogaol, [6]-dehydrogingerdione, [6]-gingerol, and [10]-gingerol of the present invention. Referring to FIGS. 1 to 4, the structures of the [6]-shogaol, [6]-dehydrogingerdione, [6]-gingerol, and [10]-gingerol are shown respectively. In the present invention, the obtained [6]-shogaol, [6]-dehydrogingerdione, [6]-gingerol, and [10]-gingerol are further analyzed by spectroscopy and stored in DMSO as a concentration of 10 mM till being used.

For further proving the efficiency of the medication in the present invention, various strains of clinical A. baumannii, being extensively drug-resistant, are randomly isolated from numbers of patients suffered from severe nosocomal infections of A. baumannii for a medication test of the present invention. Precisely, five strains of clinical A. baumannii, named AB1, AB2, AB4, AB5, AB6, are isolated from patients in Kaohsiung Medical University Hospital, 1600-bed tertiary referral medical center in Taiwan, wherein each of strains is from different clones by genotyping and collected from different samples, for example, sputum, wound pus, blood, pleural fluid, and bronchial washing. All of the five strains of A. baumannii are stored in trypticase soy broth (Difco Laboratories, Detroit, Mich.) with 20% glycerol at −80° C. until the following use.

With reference to TABLE 1, the susceptibility values of the five strains of A. baumannii to various commercial antibiotics are shown: In the present invention, the minimal inhibitory concentration (MIC) of each commercial antibiotic is determined respectively on each strain of A. baumannii via a broth micro-dilution method with LB broth reported by Nariman et al. in 2004. Since the drug-resistance standards for A. baumannii recommended by the Clinical and Laboratory Standards Institute (CLSI, 2009) are summarized in that: ampicillin/sulbactam≥32/16 μg/mL, cefepime≥32 μg/mL, ceftazidime≥32 μg/mL, ceftriaxone≥64 μg/mL, gentamicin≥16 μg/mL, meropenem≥16 μg/mL, piperacillin≥128 μg/mL, tetracycline≥16 μg/mL, ethoprim/sulfamethoxazole≥4/76 μg/mL, it suggests all of the five strains of A. baumannii share significant and extensive drug-resistance to all of the commercial antibiotics. Some of the antibiotics including ampicillin, cefazolin and cefmetazole have no MIC breakpoints according to CLSI.

TABLE 1 susceptibilities of the five strains of
A. haumannii to antibiotics (MICs, μg/ml)

| Antibotics | Strains | | | | |
|---|---|---|---|---|---|
|  | AB1 | AB2 | AB4 | AB5 | AB6 |
| Ampicillin | ≥512 | ≥512 | ≥512 | ≥512 | ≥512 |
| Ampicillin/Sulbactam | ≥32/16 | ≥32/16 | ≥32/16 | ≥32/16 | ≥32/16 |
| Cefazolin | ≥64 | ≥64 | ≥64 | ≥64 | ≥64 |
| Cefepime | ≥64 | ≥64 | ≥64 | ≥64 | ≥64 |
| Cefmetazole | ≥64 | ≥64 | ≥64 | ≥64 | ≥64 |
| Ceftazidime | ≥64 | ≥64 | ≥64 | ≥64 | ≥64 |
| Ceftriaxone | ≥64 | ≥64 | ≥64 | ≥64 | ≥64 |
| Gentamicin | ≥16 | ≥16 | ≥16 | ≥16 | ≥16 |
| Meropenem | ≥16 | ≥16 | ≥16 | ≥16 | ≥16 |
| Piperacillin | ≥128 | ≥128 | ≥128 | ≥128 | ≥128 |
| Piperacillin/Tazobactam | ≥128 | ≥128 | ≥128 | ≥128 | ≥128 |
| Tetracycline | 32 | ≥512 | ≥512 | ≥512 | ≥512 |
| Trimethoprim/Sulfamethoxazole | ≥16/320 | ≥16/320 | ≥16/320 | ≥16/320 | ≥16/320 |

In the present embodiment, $10^5$ cfu/mL of each strain of A. baumannii are prepared, and the medication test of the present invention is carried out by respectively providing the medication of the present invention and the ginger compound only to each strain of A. baumannii. In this way, the antimicrobial activities of the medication of the present invention and of the ginger compound only are monitored and recorded respectively. Precisely, the medication test of the present invention has 4 steps, including (a) [6]-shogaol step, (b) [6]-dehydrogingerdione step, (c) [6]-gingerol step, and (d) [10]-gingerol step, in order to separately analyze the antimicrobial activities of the medication with various formula of 25 μg/mL tetracycline and [6]-shogaol, 25 μg/mL tetracycline and [6]-dehydrogingerdione, 25 μg/mL tetracycline and [6]-gingerol, also 25 μg/mL tetracycline and [10]-gingerol individually.

Referring to TABLE 2, the MIC values of the medication with 25 μg/mL tetracycline and [6]-shogaol against the five strains of A. baumannii are summarized. It is suggested that the medication of the present invention, consisting of 25 μg/mL tetracycline and [6]-shogaol, shows significant antimicrobial effect against to all of the five strains of A. baumannii. Furthermore, the [6]-shogaol itself also has dramatically antimicrobial ability to the five strains of A. baumannii, with diverse MIC values from 208.1 μM to 347.2 μM on different strains of A. baumannii.

TABLE 2 antimicrobial activities of the medication (a)

| groups | [6]-shogaol only (μM) | Medication (Tetracycline + [6]-shogaol) (μM) |
|---|---|---|
| AB1 | 208.1 | <10.0 |
| AB2 | 274.0 | <10.0 |
| AB4 | 279.7 | <10.0 |
| AB5 | 261.3 | <10.0 |
| AB6 | 347.2 | <10.0 |

Referring to TABLE 3, the MIC values of the medication with 25 μg/mL tetracycline and [6]-dehydrogingerdione against the five strains of A. baumannii are summarized. It is suggested that the medication of the present invention, consisting of 25 μg/mL tetracycline and [6]-dehydrogingerdione, shows significant antimicrobial effect against to all of the five strains of A. baumannii. Furthermore, the [6]-dehydrogingerdione itself also has dramatically antimicrobial ability to the five strains of A. baumannii, with diverse MIC values from 137.6 μM to 207.1 μM on different strains of A. baumannii.

TABLE 3 antimicrobial activities of the medication (b)

| groups | [6]-dehydrogingerdion only (μM) | Medication (tetracycline + [6]-dehydrogingerdion) (μg/μM) |
|---|---|---|
| AB1 | 198.1 | <10.0 |
| AB2 | 166.2 | <10.0 |
| AB4 | 137.6 | <10.0 |
| AB5 | 178.5 | <10.0 |
| AB6 | 207.1 | <10.0 |

Referring to TABLE 4, the MIC values of the medication with 25 μg/mL tetracycline and [6]-gingerol against the five strains of A. baumannii are summarized. It is suggested that the medication of the present invention, consisting of 25 μg/mL tetracycline and [6]-gingerol, shows significant antimicrobial effect against to all of the five strains of A. baumannii. Furthermore, the [6]-gingerol itself also has dramatically antimicrobial ability to, the five strains of A. baumannii, with diverse MIC values from 226.4 μM to 277.3 μM on different strains of A. baumannii.

TABLE 4 antimicrobial activities of the medication (c)

| groups | [6]-gingerol only (μM) | Medication (tetracycline + [6]-gingerol) (μg/μM) |
|---|---|---|
| AB1 | 226.4 | <10.0 |
| AB2 | 226.8 | <10.0 |
| AB4 | 297.1 | <10.0 |
| AB5 | 277.3 | <10.0 |
| AB6 | 275.6 | <10.0 |

Referring to TABLE 4, the MIC values of the medication with 25 μg/mL tetracycline and [10]-gingerol against the five strains of A. baumannii are summarized. It is suggested that the medication of the present invention, consisting of 25 μg/mL tetracycline and [10]-gingerol, shows significant antimicrobial effect against to all of the five strains of A. baumannii. Furthermore, the [10]-gingerol itself also has dramatically antimicrobial ability to the five strains of A. baumannii, with diverse MIC values from 196.0 μM to 207.5 μM on different strains of A. baumannii.

TABLE 5 antimicrobial activities of the medication (d)

| groups | [10]-gingerol only (μM) | Medication (tetracycline + [10]-gingerol) (μg/μM) |
|---|---|---|
| AB1 | 144.6 | <10.0 |
| AB2 | 162.3 | <10.0 |
| AB4 | 196.0 | <10.0 |
| AB5 | 207.5 | <10.0 |
| AB6 | 198.1 | <10.0 |

In summary, the ginger compound of the present invention shows dramatically inhibition on all of the five strains of A. baumannii, with diverse MIC values from 132 μM to 347 μM. With the combination of the ginger compound of the present invention and tetracycline, tetracycline-resistance of the five strains of A. baumannii as it is listed in TABLE 1 can be dramatically improved. Accordingly, antimicrobial activities of ginger compound of the present invention with 25 μg/mL tetracycline are significantly effective against to A. baumannii infection. In the present invention the ginger compound is at a concentration of higher than 0 μM and lower than 10 μM.

Through the present invention, a medication comprising 25 μg/ml tetracycline and the ginger compound of the present invention is provided, wherein the ginger compound is selected from a group of [6]-shogaol, [6]-dehydrogingerdione, [6]-gingerol and [10]-gingerol, with a MIC value of <10 μM. The medication of the present invention is sufficient to suppress A. baumannii clinical infection, even for extensively drug-resistant A. baumannii, so that the medication of the present invention can prevent from clinical nosocomial infection of A. baumannii. The medication of the present invention can be manufactured into any form including a tablet, liquid powder or infection and preferable for the form of solution. In general, the medication of the present invention can be given individually or combined with other acceptable medicaments to patients suffered from severe A. baumannii infection, with the ginger compound at a preferable concentration of lower than 10 μM and higher than 0 μM.

Additionally, a new therapeutic approach for improving tetracycline-resistance of clinical A. baumannii strains is also developed by providing ginger compound of the present invention combined with tetracycline to against to A. baumannii infection. Preferably, the ginger compound of the present invention can be one of [6]-shogaol, [6]-dehydrogingerdione, [6]-gingerol, [10]-gingerol and their composition. Preferably, the tetracycline is at a concentration of 25 μg/ml and combines with one of [6]-shogaol, [6]-dehydrogingerdione, [6]-gingerol, [10]-gingerol and their composition at a concentration of lower than 10 μM and higher than 0 μM. With such approach, severe clinical A. baumannii infections, especially for extensively drug-resistant A. baumannii infections can be effectively controlled.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A method for improving tetracycline-resistance of *Acinetobacter baumannii*, by providing a medication combined with tetracycline to against *A. baumannii* infection, wherein the medication comprises [6]-dehydrogingerdione, [6]-shogaol and [6]-gingerol.

2. The method for improving tetracycline-resistance of *Acinetobacter baumannii* as defined in claim 1, wherein the medication is at a concentration of lower than 10 μM and higher than 0 μM.

3. The method for improving tetracycline-resistance of *Acinetobacter baumannii* as defined in claim 1, with the tetracycline at a concentration of 25 μg/ml.

4. A method for improving tetracycline-resistance of *Acinetobacter baumannii*, by providing a medication combined with tetracycline to against *A. baumannii* infection, wherein the medication comprises [10]-gingerol, [6]-shogaol and [6]-gingerol.

5. The method for improving tetracycline-resistance of *Acinetobacter baumannii* as defined in claim 4, wherein the medication is at a concentration of lower than 10 μM and higher than 0 μM.

6. The method for improving tetracycline-resistance of *Acinetobacter baumannii* as defined in claim 4, with the tetracycline at a concentration of 25 μg/ml.